(12) United States Patent
Baker

(10) Patent No.: US 12,059,511 B2
(45) Date of Patent: Aug. 13, 2024

(54) DISSOLVABLE COMPOSITIONS THAT INCLUDE AN INTEGRAL SOURCE OF ELECTROLYTES

(71) Applicant: Dean Baker, Cypress, TX (US)

(72) Inventor: Dean Baker, Cypress, TX (US)

(73) Assignee: Martha Elizabeth Hightower Baker, Cypress, TX (US)

( * ) Notice: Subject to any disclaimer, the term of this patent is extended or adjusted under 35 U.S.C. 154(b) by 257 days.

(21) Appl. No.: 16/385,267

(22) Filed: Apr. 16, 2019

(65) Prior Publication Data

US 2019/0314559 A1     Oct. 17, 2019

Related U.S. Application Data

(60) Provisional application No. 62/658,407, filed on Apr. 16, 2018.

(51) Int. Cl.
| | | |
|---|---|---|
| *A61L 31/16* | (2006.01) | |
| *A61L 31/02* | (2006.01) | |
| *B60R 13/00* | (2006.01) | |
| *B64C 1/00* | (2006.01) | |
| *C09K 8/70* | (2006.01) | |
| *E21B 29/02* | (2006.01) | |
| *E21B 33/12* | (2006.01) | |
| *E21B 43/26* | (2006.01) | |

(52) U.S. Cl.
CPC ............. *A61L 31/16* (2013.01); *A61L 31/028* (2013.01); *B60R 13/00* (2013.01); *B64C 1/00* (2013.01); *C09K 8/70* (2013.01); *E21B 29/02* (2013.01); *E21B 33/12* (2013.01); *E21B 43/26* (2013.01); *A61L 2420/02* (2013.01); *B64C 2001/0054* (2013.01)

(58) Field of Classification Search
None
See application file for complete search history.

(56) References Cited

U.S. PATENT DOCUMENTS

| | | |
|---|---|---|
| 3,264,073 A | 8/1966 | Schmitt |
| 3,655,425 A | 4/1972 | Longo et al. |
| 3,752,685 A | 8/1973 | Honda et al. |
| 4,303,732 A | 12/1981 | Torobin |

(Continued)

OTHER PUBLICATIONS

Aluminum, http://web.archive.org/web/20020603153546/http://www.aluminyumsanayi.com/aluwebsayfam2.html, Jun. 3, 2002, 4 pages.

(Continued)

*Primary Examiner* — Matthew R Buck
*Assistant Examiner* — Douglas S Wood
(74) *Attorney, Agent, or Firm* — Alberto Q. Amatong, Jr.; Amatong McCoy LLC

(57) ABSTRACT

A dissolvable composition is disclosed. The composition includes a first material (e.g., an anode), a second material (e.g., a cathode), and a third material (electrolytic material). The third material is reactive with water to form an electrolyte. The first material and the second material are electrochemically different such that the first material and the second material are capable of galvanic reaction in the presence of water and electrolytes. Also disclosed are tools or other apparatus made from the composition, as well as processes, systems, and apparatus for making and using such compositions, tools, and other apparatus.

18 Claims, 6 Drawing Sheets

(56) References Cited

U.S. PATENT DOCUMENTS

| | | | |
|---|---|---|---|
| 4,450,184 A | 5/1984 | Longo et al. | |
| 4,453,081 A | 6/1984 | Christ et al. | |
| 4,536,158 A | 8/1985 | Bruins et al. | |
| 4,624,865 A | 11/1986 | Gindrup et al. | |
| 4,939,038 A | 7/1990 | Inabata | |
| 5,070,591 A | 12/1991 | Quick et al. | |
| 5,271,749 A | 12/1993 | Rai et al. | |
| 5,601,924 A | 2/1997 | Beane et al. | |
| 5,786,785 A | 7/1998 | Gindrup et al. | |
| 5,892,476 A | 4/1999 | Gindrup et al. | |
| 5,965,829 A | 10/1999 | Haynes et al. | |
| 6,024,915 A | 2/2000 | Kume et al. | |
| 6,207,218 B1 | 3/2001 | Layrolle et al. | |
| 6,630,008 B1 | 10/2003 | Meeks et al. | |
| 6,656,587 B2 | 12/2003 | Johnson et al. | |
| 6,709,739 B1 | 3/2004 | Mullen et al. | |
| 6,733,503 B2 | 5/2004 | Layrolle et al. | |
| 6,752,938 B2 | 6/2004 | Wang et al. | |
| 6,831,223 B2 | 12/2004 | Kamata et al. | |
| 6,849,186 B2 | 2/2005 | Johnson et al. | |
| 6,852,272 B2 | 2/2005 | Artz et al. | |
| 6,854,172 B2 | 2/2005 | Kaese et al. | |
| 6,864,297 B2 | 3/2005 | Nutt et al. | |
| 6,919,063 B2 | 7/2005 | Jang et al. | |
| 7,498,077 B2 | 3/2009 | Joseph et al. | |
| 8,211,247 B2 | 7/2012 | Marya et al. | |
| 8,220,554 B2 | 7/2012 | Jordan et al. | |
| 8,342,094 B2 | 1/2013 | Marya et al. | |
| 8,353,604 B2 | 1/2013 | Glazier | |
| 8,409,289 B2 | 4/2013 | Truckai et al. | |
| 8,485,265 B2 | 7/2013 | Marya et al. | |
| 8,535,604 B1 | 9/2013 | Baker et al. | |
| 8,573,295 B2 | 11/2013 | Johnson et al. | |
| 8,663,401 B2 | 3/2014 | Marya et al. | |
| 8,677,903 B2 | 3/2014 | Marya et al. | |
| 8,770,261 B2 | 7/2014 | Marya | |
| 8,986,369 B2 | 3/2015 | Steckel et al. | |
| 9,068,429 B2 | 6/2015 | Mailand et al. | |
| 9,079,246 B2 | 7/2015 | Xu et al. | |
| 9,090,956 B2 | 7/2015 | Xu | |
| 9,109,429 B2 | 8/2015 | Xu et al. | |
| 9,127,515 B2 | 9/2015 | Xu et al. | |
| 9,333,099 B2 | 5/2016 | Pacetti et al. | |
| 9,353,010 B2 | 5/2016 | McEntire et al. | |
| 10,125,565 B2 * | 11/2018 | Fripp | E21B 43/16 |
| 10,156,118 B2 * | 12/2018 | Fripp | E21B 34/063 |
| 10,612,332 B1 * | 4/2020 | Sage | B64C 39/024 |
| 11,602,788 B2 * | 3/2023 | Baker | B33Y 40/10 |
| 2003/0180171 A1 | 9/2003 | Artz et al. | |
| 2004/0146543 A1 | 7/2004 | Shimp et al. | |
| 2005/0260093 A1 | 11/2005 | Artz et al. | |
| 2006/0045787 A1 | 3/2006 | Jandeska, Jr. et al. | |
| 2008/0249638 A1 * | 10/2008 | Asgari | A61F 2/28 623/23.72 |
| 2009/0074604 A1 | 3/2009 | Chen et al. | |
| 2010/0294510 A1 | 11/2010 | Holmes | |
| 2011/0135953 A1 | 6/2011 | Xu et al. | |
| 2012/0103135 A1 | 5/2012 | Xu et al. | |
| 2012/0141775 A1 | 6/2012 | Ahmed et al. | |
| 2013/0032357 A1 * | 2/2013 | Mazyar | E21B 34/063 166/376 |
| 2013/0098203 A1 | 4/2013 | Sherman et al. | |
| 2014/0004270 A1 | 1/2014 | Sherman et al. | |
| 2014/0202708 A1 | 7/2014 | Jacob et al. | |
| 2014/0228972 A1 | 8/2014 | Xu | |
| 2014/0251641 A1 | 9/2014 | Marya et al. | |
| 2014/0286810 A1 | 9/2014 | Marya et al. | |
| 2014/0363693 A1 | 12/2014 | Tamiya et al. | |
| 2016/0320769 A1 * | 11/2016 | Deffenbaugh | E21B 23/10 |
| 2017/0072465 A1 | 3/2017 | Welch et al. | |
| 2017/0072471 A1 | 3/2017 | Welch et al. | |
| 2017/0281827 A1 | 10/2017 | Baker | |
| 2019/0314559 A1 * | 10/2019 | Baker | A61L 31/148 |
| 2019/0368301 A1 * | 12/2019 | Eitschberger | E21B 33/068 |

OTHER PUBLICATIONS

Materials Aluminum Oxide (A1203) Properties, May 20, 2006, http://web.archive.org/web/20060520195437/ http://accuratus.com/alumox.html, 3 pages.

Mordike et al, Magnesium Properties—applications—potential, 2001, Elsevier, Materials Science and Engineering A, vol. 302, pp. 37-45.

Engineering ToolBox, (2003). Electrode Potential and Galvanic Corrosion. [online] Available at: https://www.engineeringtoolbox.com/electrode-potential-d_ 482.html; accessed Jul. 24, 2020. [3 pages].

* cited by examiner

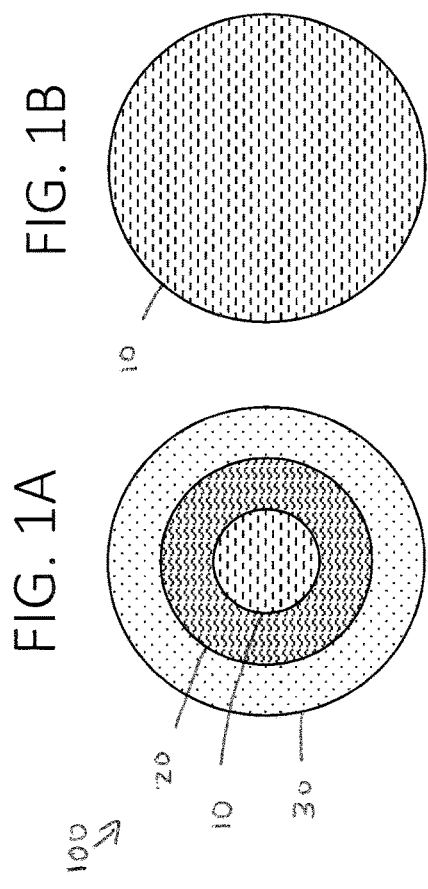
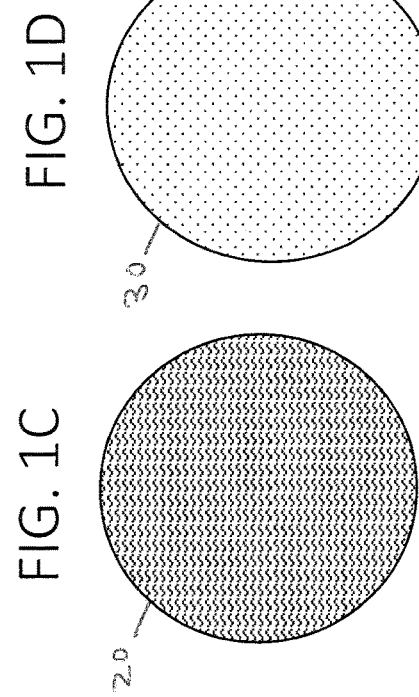
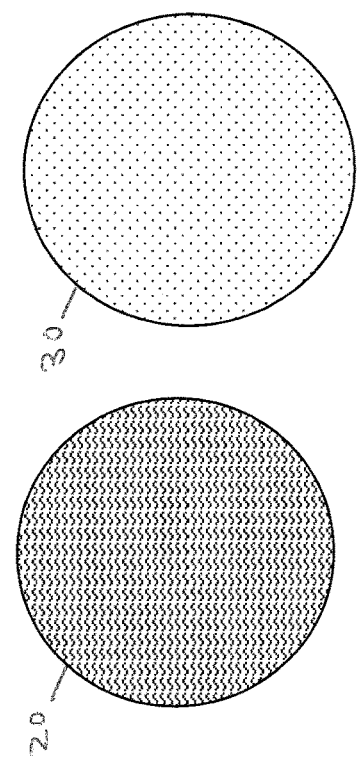
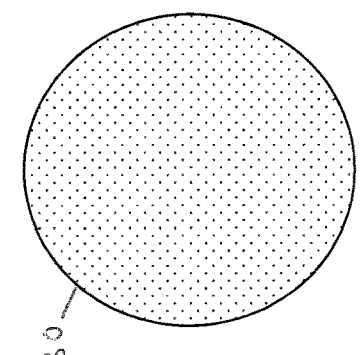
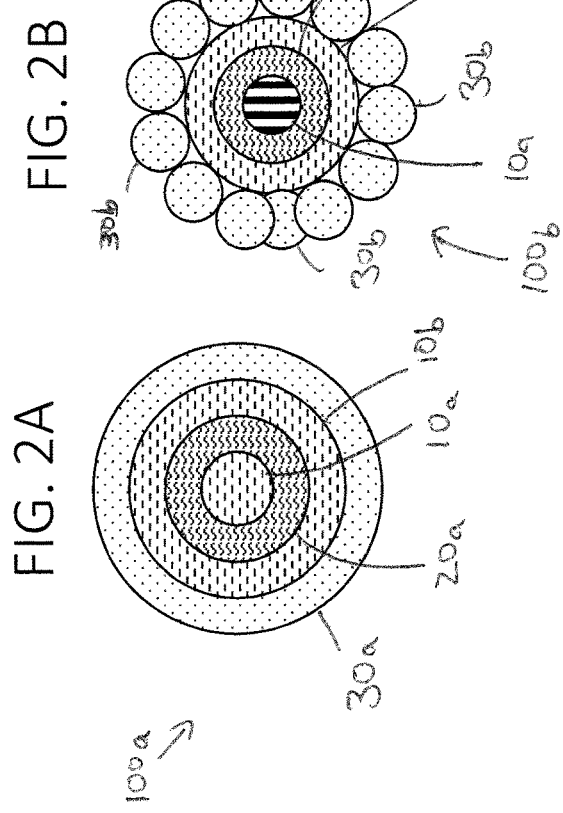
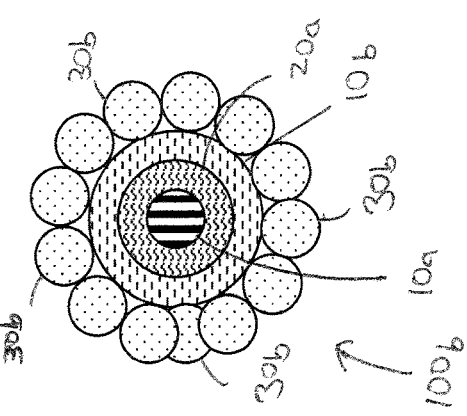
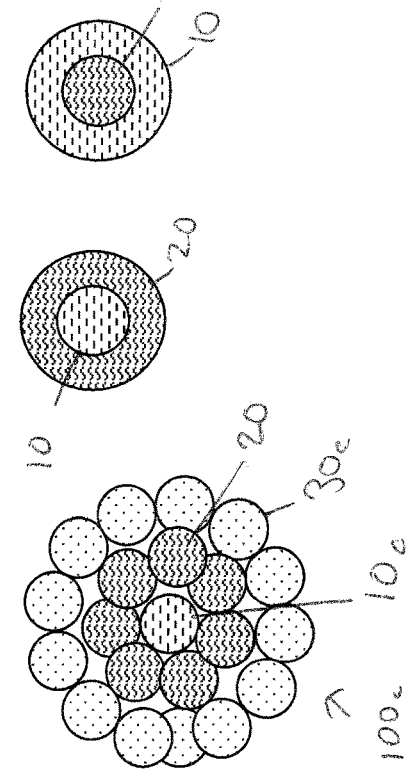
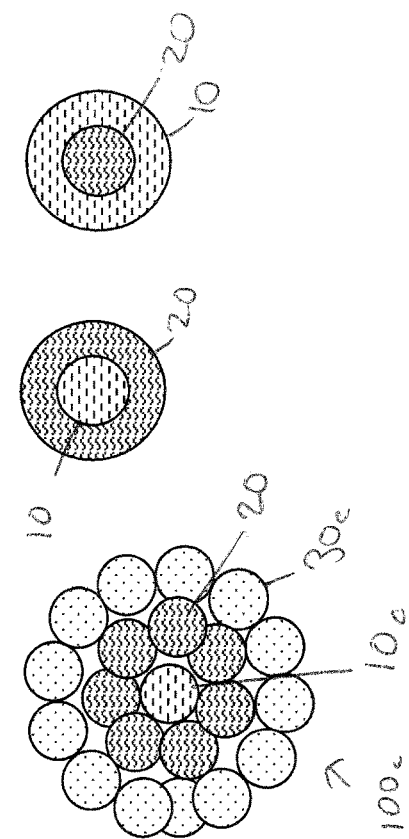
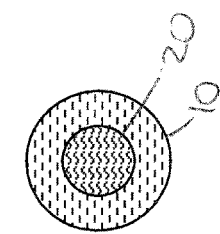

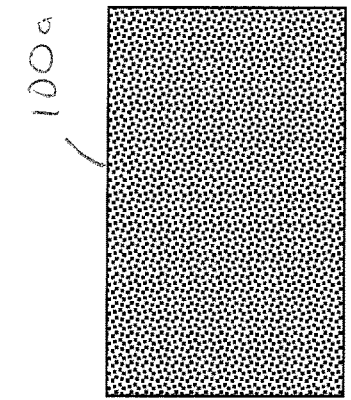
FIG. 2D
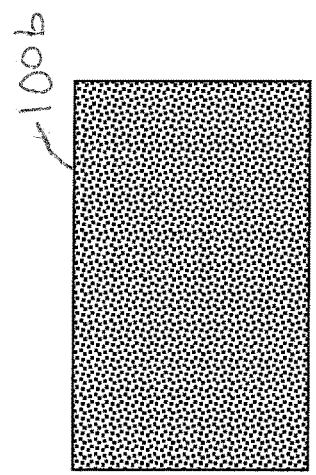
FIG. 2E
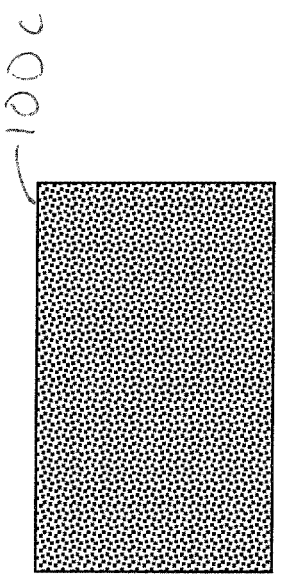
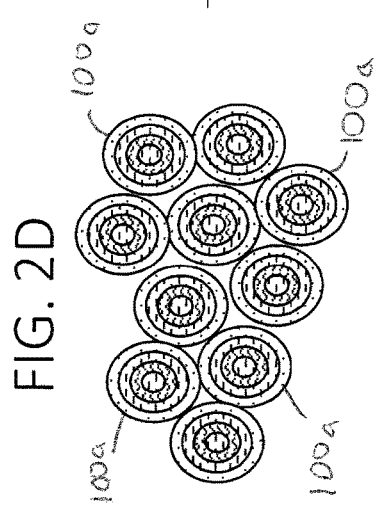
FIG. 2F
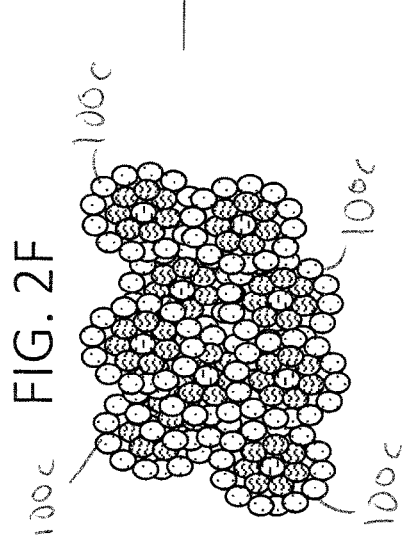

DISSOLVABLE COMPOSITIONS THAT INCLUDE AN INTEGRAL SOURCE OF ELECTROLYTES

CROSS-REFERENCE TO RELATED APPLICATIONS

The present application claims the benefit of U.S. Provisional Patent Application No. 62/658,407, filed on Apr. 16, 2018, the entirety of which is incorporated herein by reference.

FIELD

The present disclosure relates to dissolvable compositions and tools or other apparatus made therefrom, as well as to processes, systems, and apparatus for making and using such compositions, tools, and other apparatus. More particularly, the present disclosure relates to dissolvable compositions that include an integral source of electrolytes.

BACKGROUND

In certain applications it is beneficial to use a tool and apparatus that is dissolvable or otherwise degradable, such as to avoid the necessity to retrieve the tool or apparatus after use, to reduce or eliminate the risk of others retrieving the tool or apparatus after use, and/or to increase the efficiency and effectiveness of an operation within which the tool or apparatus is used.

Some industries utilize materials that dissolve or otherwise degrade via galvanic reaction. Galvanic reaction requires a liquid (e.g., water) with an electrolytic component contained therein for use in starting and controlling the galvanic reaction. For example, in the oil and gas industry, dissolvable tooling typically requires a liquid having an electrolytic additive therein to form a reactive media for galvanic reactions. To achieve this, typically large proportions of electrolytic additive (e.g., KCl or HCl) are added directly to the water (e.g., drilling fluid or mud). For example, from three (3) to four (4) pounds of such an electrolytic additive is typically added for every gallon of liquid. In many drilling applications, this may require the addition of, for example, thirty thousand (30,000) pounds of electrolytic additive to the liquid, given the large volumes of fluid in such a downhole environment. As only a relatively small number of electrolytes are in proximity to the dissolvable tooling, with the remainder spread throughout the liquid, much of the electrolytic additive is wasted (i.e., not directly active in the galvanic reaction).

BRIEF SUMMARY

One aspect of the present disclosure provides for a dissolvable composition that includes a first material, a second material, and a third material. The third material is reactive with water to form an electrolyte. The first material and the second material are electrochemically different such that the first material and the second material are capable of galvanic reaction in the presence of water and electrolytes.

Another aspect provides for a method of forming such a composition.

A further aspect provides for a method of forming a dissolvable composition. The method includes providing a dissolvable composition. The method includes providing a core particle, applying one or more coatings to the core particle, and mixing an electrolytic material with the coated core particle or coating an electrolytic material onto the coated core particle. The core particle and the coating(s) are electrochemically different such that the core particle and the coating(s) are capable of galvanic reaction in the presence of water and electrolytes.

Another aspect relates to a method of making a dissolvable article. The method includes providing a dissolvable composition, and forming an article from the dissolvable composition.

Some aspects provide for an article of manufacture composed of a dissolvable composition.

One aspect provides for a method of hydraulic fracturing that includes providing frac balls downhole. The frac balls are composed of a dissolvable composition. The method includes at least partially fluidically blocking perforations in the wellbore downhole with the frac balls. Upon contact with the liquid downhole, the electrolytic material begins to disassociate into ions and the anode and cathode materials begin to galvanically react with one another, such that the frac balls dissolve. As used herein, "fluidically blocking" a perforation refers to preventing or at least impairing fluid flow through the perforation. As used herein, "fluidically unblocking" a perforation refers to allowing fluid flow through a previously blocked perforation.

A further aspect provides for a method of using a drone composed of the dissolvable composition. The method includes flying the drone to a desired location, flying the drone into water, and allowing the drone to dissolve in the water. Upon contact with the liquid, the electrolytic material begins to disassociate into ions and the anode and cathode materials begin to galvanically react with one another, such that the drone dissolves.

An additional aspect provides for a system for making a dissolvable composition. The system includes one or more fluidized bed reactors configured for chemical vapor deposition of one material onto another, and optionally one or more solid-state manufacturing apparatus.

Another aspect of the present disclosure provides for a dissolvable downhole component that includes a dissolvable body composed of a plurality of particles bonded together. The plurality of particles include at least first and second materials that are electrochemically incompatible, including an anode and cathode system, and a third material that is an electrolytic material selected to accelerate galvanic reaction between the first and second materials.

Another aspect provides for a method that includes at least partially fluidically blocking a perforation in a wellbore with a frac ball that is composed of a dissolvable composition. The dissolvable composition includes a first material, a second material, and a third material. The third material is reactive with water to form an electrolyte, and the first material and the second material are electrochemically different such that the first material and the second material are capable of galvanic reaction in the presence of water and electrolytes. The method includes hydraulically fracturing the wellbore. The method includes fluidically unblocking the perforation by dissolving the frac ball. Dissolving the frac ball includes contacting the frac ball with water. Upon contact of the frac ball with water, the third material begins to disassociate into ions and the first and second materials begin to galvanically react with one another.

BRIEF DESCRIPTION OF THE DRAWINGS

So that the manner in which the features and advantages of the systems, products, and/or methods so of the present disclosure may be understood in more detail, a more particular description briefly summarized above may be had by reference to the embodiments thereof which are illustrated in the appended drawings that form a part of this specification. It is to be noted, however, that the drawings illustrate only various exemplary embodiments and are therefore not to be considered limiting of the disclosed concepts as it may include other effective embodiments as well.

FIG. 1A depicts a particle of the composition in accordance with certain aspects of the present disclosure;

FIG. 1B depicts an anode particle of the composition in accordance with certain aspects of the present disclosure;

FIG. 1C depicts a cathode particle of the composition in accordance with certain aspects of the present disclosure;

FIG. 1D depicts an electrolytic particle of the composition in accordance with certain aspects of the present disclosure;

FIG. 2A depicts a particle of the composition in accordance with certain aspects of the present disclosure;

FIG. 2B depicts a particle matrix of the composition in accordance with certain aspects of the present disclosure;

FIG. 2C depicts another particle matrix of the composition in accordance with certain aspects of the present disclosure;

FIG. 2D depicts a plurality of particles in accordance with FIG. 2A being consolidated into a composition in accordance with the present disclosure;

FIG. 2E depicts a plurality of particles in accordance with FIG. 2B being consolidated into a composition in accordance with the present disclosure;

FIG. 2F depicts a plurality of particles in accordance with FIG. 2C being consolidated into a composition in accordance with the present disclosure;

FIG. 3A depicts a particle of the composition in accordance with certain aspects of the present disclosure;

FIG. 3B depicts a particle of the composition in accordance with certain aspects of the present disclosure;

Figure 4A:
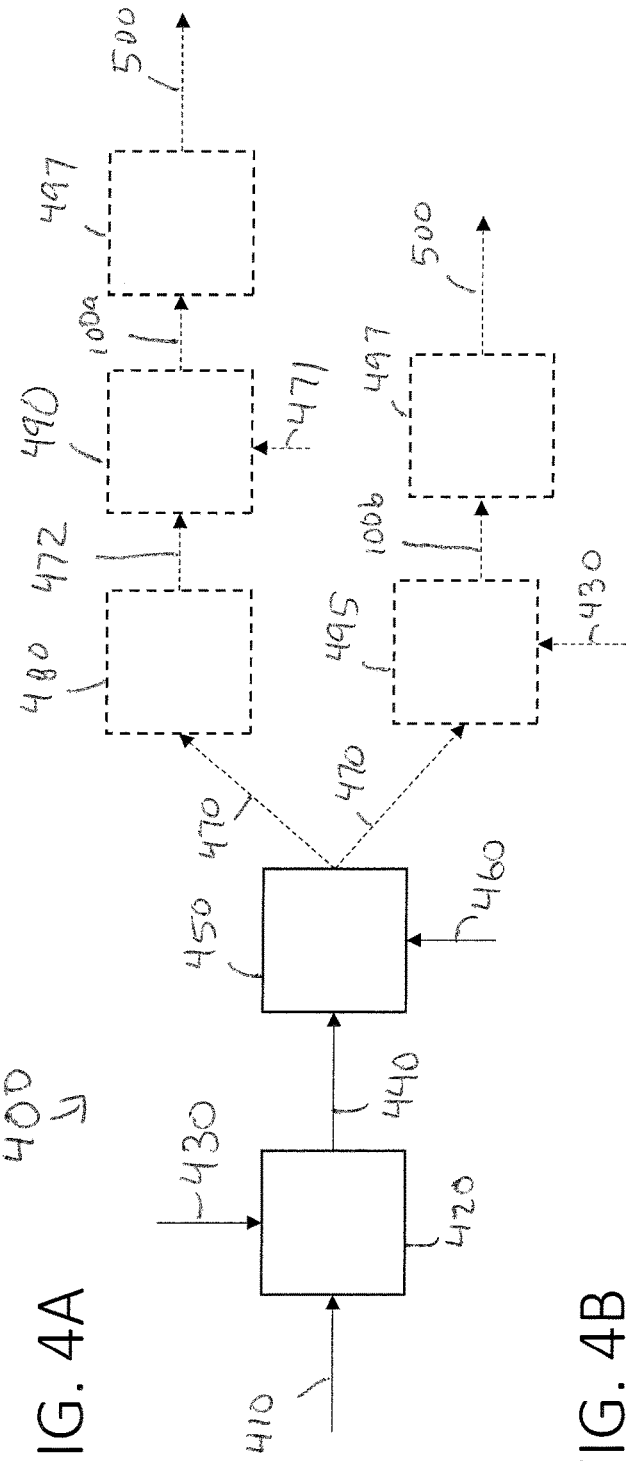
FIG. 4A depicts a system of forming a composition in accordance with certain aspects of the present disclosure, including apparatus for coating particles and a solid-state processing apparatus for consolidating particles.

Products, systems, and methods according to present disclosure will now be described more fully with reference to the accompanying drawings, which illustrate various exemplary embodiments. Concepts according to the present disclosure may, however, be embodied in many different forms and should not be construed as being limited by the illustrated embodiments set forth herein. Rather, these embodiments are provided so that this disclosure will be thorough as well as complete and will fully convey the scope of the various concepts to those skilled in the art and the best and preferred modes of practice.

DETAILED DESCRIPTION

Certain aspects of the present disclosure include dissolvable compositions and tools or other apparatus made therefrom, as well as to processes, systems, and apparatus for making and using such compositions, tools, and other apparatus. The dissolvable composition provides the ability to induce galvanic reactions without having to add additional chlorides or other electrolytes to water, and without requiring the presence of electrolytes in the water prior to addition of the dissolvable composition to the water.

Composition

One aspect of the present disclosure relates to solid compositions that are dissolvable or otherwise degradable in environments that contain liquid (e.g., water). With reference to FIGS. 1A-1D, the composition 100 includes at least three components, including: (1) anode material 10; (2) cathode material 20; and (3) electrolytic material 30.

Anode material 10 and cathode material 20 are at least two dissimilar materials that are, potentially, galvanically reactive (galvanic reactive materials), such that anode material 10 and cathode material 20 react, in certain environmental conditions, via an anode and cathode reaction.

Electrolytic material 30 may be a liquid-reactive material that, under certain environmental conditions in the presence of liquid (water or other liquid), provides electrolytes to originate the galvanic reaction between anode material 10 and cathode material 20. In some aspects, electrolytic material 30 provides electrolytes that originate the galvanic reaction and additional electrolytes that accelerate the galvanic reaction. In certain aspects, electrolytic material 30 provides the only electrolytes that originate and/or accelerate the galvanic reaction. For example, electrolytic material 30 may disassociate into constituent ions upon contact with water (e.g., via dissolving of electrolytic material 30 within the water).

In FIG. 1A, a single particle of composition 100 is shown as a layered particle, including a core particle of anode material 10, an inner layer coating of cathode material 20 about the outer circumference of anode material 10, and an outer layer coating of electrolytic material 30 about the outer circumference of cathode material 20. However, composition 100 in not limited to this particular arrangement of layers. In some aspects, the cathode material forms the core particle and the anode material forms a coating layer. Furthermore, in some aspects one or more of the component materials of the composition may be provided as separate particles, rather than as coating layers or core particles. Each component material of composition 100, including anode material 10, cathode material 20, and electrolytic material 30, is soluble in water. Thus, the dissolvable composition 100 provided herein may be formed of a core particle with a single coating or with multiple coatings. FIG. 1A depicts only a single particle of composition 100. However, composition 100 may include a plurality of such particles. In some embodiments, composition 100 includes a plurality of identical such particles. In other embodiments, composition 100 includes a plurality of particles that are a mixture of particles that differ in at least one respect (e.g., variations in ordering of layers, composition of layers, or other differences).

In some embodiments, the dissolvable composition 100 includes a plurality of particles (encapsulated or not) bonded together by various manufacturing processes requiring heat and/or pressure or using additive manufacturing methods. U.S. patent application Ser. No. 15/464,226 provides background relevant to certain aspects of the present disclosure and is incorporated herein by reference in its entirety. In particular, paragraphs [0096]-[0107] of U.S. patent application Ser. No. 15/464,226 discuss additive manufacturing techniques. Also, U.S. patent application Ser. No. 15/464,226, discusses various tool and devices, including medical implements, that may be constructed from the present disclosure. The plurality of the particles are constructed of at least two materials that are electrochemically incompatible, including an anode and cathode system in a suitable environment. Encapsulating coatings at the powder (particle) level enables for control of the reactions of both the anode and cathode materials, and promotes compatibility during the consolidation of the materials. The galvanic potentials of the first and second materials are configured to control the reaction timing of the two materials.

With the anode and cathode materials constituting the first and second materials (or the second and first materials), a third material (electrolytic material) of the dissolvable composition 100, with or without encapsulation coating(s), acts as an accelerator of the galvanic reaction. The third material may be a chloride-based salt, with Na, Ca, K, or another such salt. The third material is reactive with a wellbore fluid to aid in the formation of an electrolyte (e.g., via dissolution of the third material into cations and anions). In some aspects, the third material is highly reactive with fluids, including: drilling mud, oil, distilled water, tap water, natural gas, or combinations thereof; thereby, enabling the start and acceleration of reaction of the first and second materials. The water in which the dissolvable composition dissolves may be water from any of numerous sources of water, including lake water, ground water, river water, ocean water, pond water, ditch water, rain water, puddle water, or another source of water.

In some aspects, the difference in chemical electrical potential between the first material and the second material is such that the total time required to dissolve the dissolvable composition 100 is substantially controlled by encapsulation coatings applied to one or more of the three reactive materials.

In some aspects, the reaction (dissolution into ions) of the third material in the presence of a wet environment functions to expose the second material to the wet environment (e.g., a downhole environment), and the reaction of the second material functions to expose the first material to the wet environment. The dissolvable composition 100 may be in the form of a matrix material (e.g., a mixture of the materials), a single or plurality of particles (e.g., a coated particle including two or more of the materials), or some combination thereof. In some aspects, the reaction of the third material functions to expose both the second and first materials to liquid (e.g., wellbore fluids).

In certain aspects, control of reaction timing of the third material is proportional to encapsulation thickness of the layers of the third material encasing the second material, and control of the reaction timing of the first material is proportional to a thickness of a shell of the second material encasing the first material.

In some aspects, each of the first material and second material (e.g., anode material 10 and cathode material 20) may include: magnesium, aluminum, zinc, titanium, iron, tungsten, refractory metals, nickel, calcium, potassium, sodium alloys thereof, ceramics thereof, or combinations of the aforementioned. In some aspects, at least one of the first material and second material are unalloyed. Encapsulation of the materials may function to control the reaction rate thereof.

In certain aspects, the reactivity of the material (or tool made therefrom) and rate of reaction is a function of the particle sizes of the first, second and third materials, temperature, pressure, pH, electrical potential, thickness of the material layers, porosity of the materials, density of the materials, or combinations thereof.

In some aspects, the composition (or tool made therefrom) is designed and controlled to dissolve within a selected period of time, which may vary from hours (less than a day), to days (less than a week), to weeks depending on the environmental conditions (e.g., liquid, temperature, pressure, etc.) and desired outcomes.

Composition—Anode

Anode material 10 may be a material, compound, molecule, or element capable of undergoing a galvanic reaction with cathode material 20. Anode material 10 may be or include a metal or alloy capable of providing a positive ion. For example, and without limitation, anode material 10 may be or include Mg or an alloy thereof, Al or an alloy thereof, Zn or an alloy thereof, Cu or an alloy thereof, or another metal or alloy capable of providing a positive ion.

In some aspects, the anode material is from 60 to 98.5 weight percent (wt. %), or from 70 to 90 wt. %, or from 75 to 85 wt. % of the composition, based on the total weight of the composition.

Composition—Cathode

Cathode material 20 may be a material, compound, molecule, or element capable of undergoing a galvanic reaction with anode material 10. Cathode material 20 may be or include a metal or alloy capable of providing a negative ion. For example, and without limitation, cathode material 20 may be or include Ni or an alloy thereof, Fe or an alloy thereof, Ti or an alloy thereof, a refractory metal (e.g., W, Ta, Mo) or an alloy thereof, or another metal or alloy capable of providing a negative ion.

In some aspects, the cathode material is from 0.5 to 30 wt. %, or from 2 to 25 wt. %, or from 5 to 20 wt. %, or from 8 to 16 wt. %, or from 10 to 12 wt. % of the composition, based on the total weight of the composition.

Composition—Electrolyte

Electrolytic material 30 may be an acid former, or another material capable of forming or providing electrolytes upon contact with certain liquids, such as water. For example, electrolytic material 30 may be a salt, such as an alkali metal salt or an alkaline earth metal salt. In some aspects, electrolytic material 30 may be a chloride, an oxide, or a nitride. For example, and without limitation, electrolytic material 30 may be NaCl, CaCl, KCl, MgCl, or HCl.

Electrolytic material 30 is a water-reactive material, such that upon contact with water, electrolytic material 30 forms or provides electrolytes (e.g. via dissolution within the water int ions). As the presence of electrolytes are necessary for the propagation of a galvanic reaction, the formation or provision of electrolytes by electrolytic material 30 originates and/or accelerates the galvanic reaction between the anode material 10 and cathode material 20; thereby, originating and/or accelerating the degradation (e.g., dissolution) of composition 100.

The presence of electrolytic material 30 as an integrated component of composition 100 eliminates the requirement of adding (preloading) an electrolytic material into the liquid of the environment within which the composition 100 is to be dissolved, and eliminations the requirement of the water having electrolytes present therein prior to addition of composition 100. Furthermore, because electrolytic material 30 is integrated into composition 100, a concentrated population of electrolytic material 30 is located in localized proximity to both anode material 10 and cathode material 20. As such, the initiation and reaction rate of the galvanic reaction between anode material 10 and cathode material 20 is accelerated. That is, when electrolyte is added separately to the water, the electrolyte dissolves therein, spreading in an even distribution within the water. However, when the electrolyte is an integral part of composition 100, then, for at least a period of time, the electrolyte is more highly concentrated at or proximate the remainder of composition 100 in comparison to the concentration of the electrolyte at other locations throughout the water.

Furthermore, the localized proximation of electrolytic material 30 allows for localized control of the pH of the reactive environment (of the water, at least the water proximate the dissolving composition). Without being bound by theory, it is believed that HCl or other acids may be formed as a result of dissolution of electrolytic material 30 into the water of the surrounding environment. This HCl or other acid decreases the pH of the local environment within which the reaction is occurring, preventing or reducing the occurrence of the pH from increasing above 11. At a pH of above 11, the galvanic reaction may cease to occur. As such, the electrolytic material 30 may function, at least in part, as a pH controller by providing/forming acid, preventing the pH from increasing above 11. In some aspects, the pH of the surrounding environment, or at least the localized environment, within which the galvanic reaction occurs is maintained from 0 to 11, or from 1 to 10, or from 2 to 9, or from 3 to 8, or from 4 to 7, or from 5 to 6.

With the electrolytic material 30 as an integrated component of composition 100, galvanic, reaction between anode material 10 and cathode material 20 may occur at various temperatures and without preloading the environmental liquid with a chloride or other electrolyte. Thus, degradation (e.g., dissolution) of composition 100 will commence and continue to its conclusion without requiring the addition of an electrolyte into the liquid environment surrounding composition 100. Furthermore, as electrolytic material 30 is present in the localized environment within which the galvanic reaction occurs, a smaller amount of electrolytic material 30 is required to be used, relative to the amount of electrolytic material that would be required to be added to the liquid as a separate addition. For example, in an application that would typically require the addition of approximately thirty thousand (30,000) pounds of KCl or other electrolytic material into the water of the surrounding environment to initiate and provide for the galvanic reaction, by providing the electrolytic material as an integral component of the dissolvable composition 100 (e.g., a layer thereof) the amount of electrolytic material required can be reduced to approximately thirty-two (32) pounds. While not being bound by theory, it is believed that this is at least partially a result of electrolytic material 30 being in close physical proximity to anode material 10 and cathode material 20 when dissolving. In some aspects, reaction of a relatively small amount of electrolytic material 30 functions to accelerate reaction of anode and cathode materials (10, 20) in a liquid environment.

In certain aspects, the galvanic reaction between anode material 10 and cathode material 20, in the presence of water and electrolytic material 30, will be capable of occurring at a range of temperatures, including below room temperature, at room temperature, and above room temperature. For example, the galvanic reaction between anode material 10 and cathode material 20, in the presence of water and electrolytic material 30, may occur at temperatures ranging from 60 to 350° F., or from 80 to 330° F., or from 100 to 310° F., or from 120 to 290° F., or from 140 to 270° F., or from 160 to 250° F., or from 180 to 240° F., or from 200 to 220° F.

Furthermore, as electrolytic material 30 provides electrolytes into the local environment, the galvanic reaction of composition 100 may occur by placing composition 100 within distilled water or other water lacking electrolytes or water containing insufficient electrolytes to initiate the galvanic reaction. While the galvanic reaction of composition 100 may occur without the addition of electrolytes to the water (other than electrolytic material 30 integrated into the composition), in some aspects an additional, non-integrated electrolytic material may be added into the liquid environment (e.g., KCl).

As the galvanic reaction initiation and propagation is sped up by using dissolvable composition 100 having integrated electrolytic material 30, the time frame within which composition 100 dissolves is shortened. Shortening the amount of time required to dissolve composition 100 can, in many applications, substantially increase the financial efficiency of an operation. For example, in an operation in which removal of a frac ball is required, the time spent removing the frac ball is time that could otherwise be spent producing oil or gas from the associated well. Shortening this timeframe would allow a well operator to begin producing oil or gas sooner, e.g., within hours or days, rather than within tens of days (e.g., within 40 to 45 days). This can be significant, as some wells may produce hundreds of thousands of U.S. dollars in revenue per day, turning a financially unfeasible operation into a financially feasible operation.

In some aspects, the electrolytic material forms from 0.5 to 35 wt. %, or from 2 to 30 wt. %, or from 5 to 25 wt. %, or from 10 to 20 wt. %, or from 12 to 16 wt. % of the composition, based on the total weight of the composition.

Composition—Exemplary Arrangements

With reference to FIG. 2A, an exemplary arrangement of layers for a particle of composition 100a is shown. In some aspects, Mg used herein has a compression strength of up to about 60,000 or 65,000 psi. In some aspects, Al used herein has a compression strength of up to about 65,000 to 75,000 psi. In some aspects, Ti used herein has a compression strength of up to about 200,000 psi. In some aspects, Ni used herein has a compression strength of up to about 250,000 psi.

Composition 100a includes an anode material core 10a, such as an Mg-core. The anode material core 10a is coated with a cathode material coating layer 20a, such as a coating layer of Ni. Cathode material coating layer 20a is coated with anode material coating layer 10b, such as a coating layer of Al. Anode material coating layer 10b is coated with electrolytic material coating layer 30a, such as a coating layer of a chloride salt.

FIG. 2B depicts an alternative embodiment where, rather than coating electrolytic material onto the other components of the dissolvable composition, electrolytic material 30b is mixed, as separate particles, with the other components of the dissolvable composition 100b, as shown in FIG. 2B. In some aspects, electrolytic material 30b particles are coated with one or more layers, such as layers of Ni, Cu, Al, or Mg. The coating on electrolytic material 30b particles may be a continuous coating or a partial coating. Electrolytic material 30b particles may have a diameter of from 80 to 105 microns, such as about 50 microns, for example.

In the embodiments shown in FIGS. 2A and 2B, the anode material core forms from 70-90 wt. % of the composition, the cathode material coating forms from 0.5 to 25 wt. % of the composition, the anode material coating forms from 0.5 to 25 wt. % of the composition, and the electrolytic material forms from 0.5 to 30 wt. % of the composition. Within the composition, the Al coating layers facilitate bonding between adjacent Ni coating layers and chloride salt layers. Also, Al coating layers may be used as a second anode material coating layer. Additionally, Al coating layers provide additional strength to the particle of the dissolvable composition.

FIG. 2C depicts an embodiment of composition 100c where each of anode material 10c, cathode material 20c, and electrolytic material 30c are mixed together as separate particles, rather than being coated onto one another.

FIG. 3A depicts another exemplary arrangement of layers for use in the composition. In the embodiment shown in FIG. 3A, an anode material core 10, such as Mg-core, is coated with a cathode material coating layer 20, such as a Ni coating layer. The Ni coating layer may be replaced with, for example, an Fe coating layer (cathode). FIG. 3B depicts another exemplary arrangement of layers for use in the composition. In the embodiment shown in FIG. 3B, a cathode material core 20, such as a Ni core, is coated with an anode material coating layer 10, such as Mg coating layer. The Ni core may be replaced with, for example, an Fe core. Each of the particles in FIGS. 3A and 3B may be mixed with or coated with an electrolytic material.

In any of the embodiments shown and/or described herein, the ordering of the anodes and cathodes may be reversed. For example, some embodiments include an anode core with a cathode coating layer. In other embodiments a cathode core includes an anode coating layer. The wider the potential gap between the anode and cathode materials, the faster the galvanic reaction will proceed.

In any of the embodiments shown and/or described herein, the core particle may have a diameter ranging from about 1 to about 200 microns, or from about 50 to about 100 microns.

In any of the embodiments of the composition shown and/or described herein, the composition may be processed via any number of materials processing techniques to form articles of manufacture or precursors thereof, such as via press-forging, extruding, additive manufacturing, casting, or other solid-state processing techniques. U.S. patent application Ser. No. 14/948,204 provides certain relevant disclosure and is hereby incorporated by reference in its entirety. In particular, U.S. patent application Ser. No. 14/948,204 discloses various material forging techniques suitable for use herein, including the dynamic forging discussed beginning at paragraph [0039]. U.S. Pat. No. 8,535,604 provides certain relevant disclosure and is hereby incorporated by reference in its entirety. In particular, U.S. Pat. No. 8,535,604 discloses various solid-state processing techniques suitable for use herein, including those discussed with reference to FIG. 4.

FIGS. 2D-2F depict the consolidation of the compositions of FIGS. 2A-2C, respectively. For each of compositions 100a-100c, a plurality of particles of the composition are subjected to consolidation 200 to form bulk matrix materials 100a-100c, respectively, such as via an additive manufacturing technique or other particle consolidation technique.

Methods and Systems for Forming the Composition

Figure 4B:
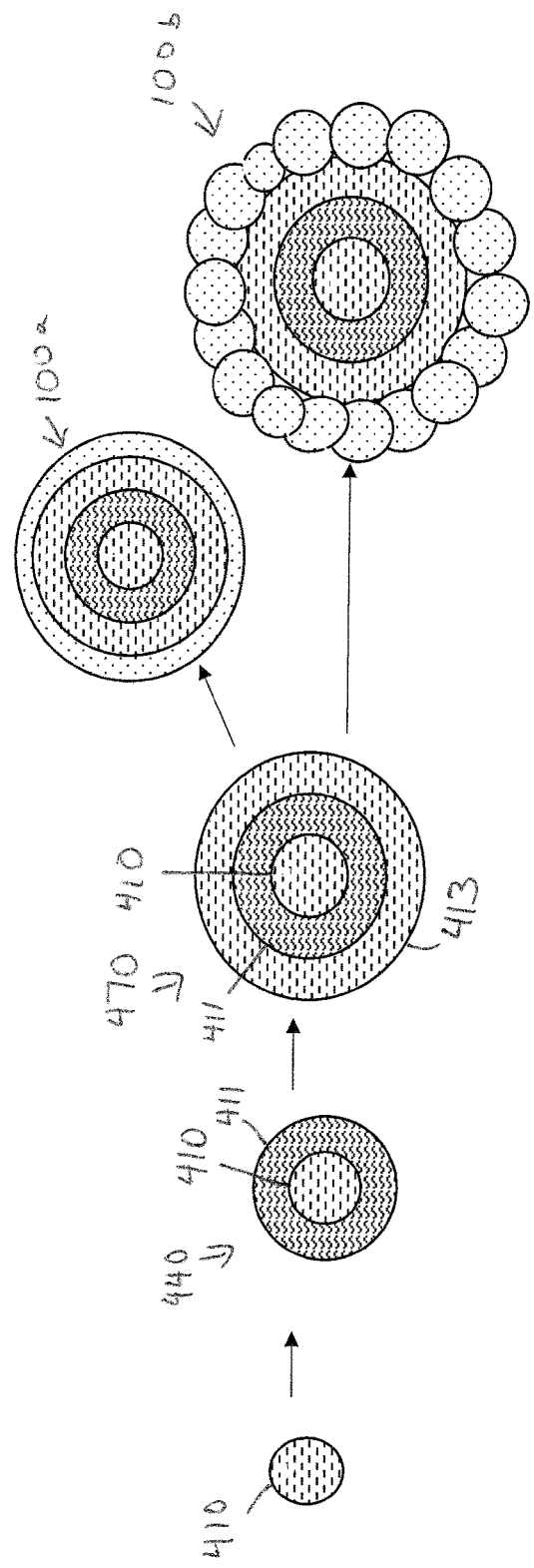
FIG. 4B depicts the production of a composition from particles and coatings in accordance with the system of FIG. 4A.

Some aspects relate to methods and systems for forming a dissolvable composition. The methods and systems may be used to form any of the embodiments of dissolvable compositions described herein. FIG. 4A depicts system 400 for forming the dissolvable composition, and FIG. 4B depicts the progression of constituent materials, as they are combined together to form the dissolvable composition in accordance with FIG. 4A. With reference to FIGS. 4A and 4B, system 400 and methods for forming the dissolvable composition will now be described.

Generally, the composition may be formed by providing a core particle and applying one or more coatings to the core particle, such as via chemical vapor deposition of the coatings onto the core particle within a fluidized bed reactor. The dissolvable composition provided herein may be formed of a core particle with a single coating or with multiple coatings.

A particular embodiment having a Mg-core, with successive coatings of Ni and Al will now be described. However, one skilled in the art would understand that the same or a similar process may be used to form other embodiments of the dissolvable composition provided herein.

Mg-core particle 410 is provided, which may be formed of Mg or an alloy thereof. Mg-core particle 410 is input into a reactor 420 for application of a coating thereon. Reactor 420 may be a fluidized bed reactor. A first, inner coating layer is applied to Mg-core particle within reactor 420. In this particular embodiment, a Ni-coating is applied to the Mg-core. A Ni-based reactant 430 is input into reactor 420. The Ni-based reactant 430 may be, for example and without limitation, nickel carbonyl. The temperature within reactor 420 ranges from 80° C. to about 150° C. Within this temperature range, Ni separates (disassociates) from the carbonyl, and the Ni deposits within reactor 420 onto the Mg-core via chemical vapor deposition (CVD).

The product 440 formed in reactor 420 includes core particle 410 with coating layer 411 of Ni, which is then transmitted to second reactor 450. Second reactor 450 may also be a fluidized bed reactor. An Al-based reactant 460 is input into second reactor 450. The Al-based reactant 460 may be, for example and without limitation, triethyl aluminum. The temperature within second reactor 450 ranges from 200° C. to 440° C. Within this temperature range, Al separates (disassociates) from the ethyl groups, and the Al deposits within reactor 450 onto the Ni-coating via chemical vapor deposition (CVD).

The product 470 of the second reactor 450, which includes an Al coating layer 413 on product 440, is then coated or mixed with the electrolytic material. To coat product 470, product 470 is transmitted to third reactor 480 where a coating of a metal capable of forming an electrolyte is applied (e.g., Na, Ca, K, Mg). This coating may be applied via plating (electroplating) or CVD, forming product 472. Chlorine 471 may then be passed over the material in fourth reactor 490 to react and form the electrolyte (e.g., NaCl, CaCl, KCl, MgCl), forming composition 100a. The product may then, optionally, be coated with an additional layer of Al (not shown).

To mix product 470, product 470 is transmitted to mixer 495, which may be a V-blender or ball mill, where product 470 is mixed with an electrolytic material 430.

Either by mixing or coating, final dissolvable composition 100a or 100b is formed, particles of which may be solid-state processed or otherwise consolidated to form an apparatus or tool 500, such as in solid-state process system 497. In some aspects, the solid-state processing includes casting spark plasma sintering (SPS), additive manufacturing, hot isostatic pressing (HIP), or any of the other processing techniques described elsewhere herein. Thus, particles of composition 100 are consolidated together into a matrix material that may be in the form of article 500, or may be subsequently processed into article 500.

Figure 4D:
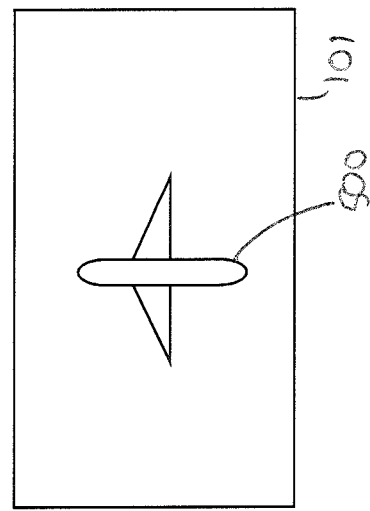
FIG. 4D depicts a wrapped embodiment of an article formed of the composition.
Figure 4C:
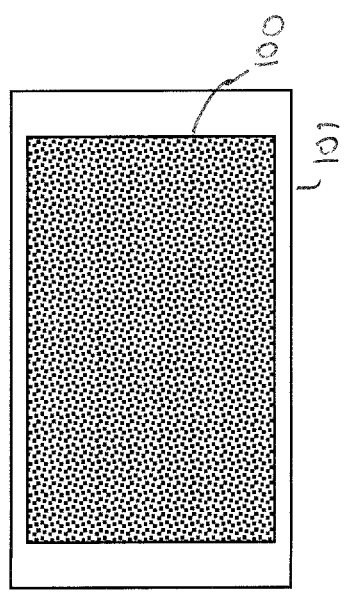
FIG. 4C depicts a wrapped embodiment of the composition.

In some aspects, due to the reactivity of the composition to moisture, the composition must be bagged or otherwise sealed and/or insulated from the environment, as ambient moisture within the air may cause the galvanic reaction to begin. For example, FIG. 4C depicts composition 100 within sealed package 101, and FIG. 4D depicts article 500 within sealed package 101.

Tools and Other Apparatus

Some aspects of the present disclosure relate to solid dissolvable tools or apparatus, such as downhole tools, that are capable of reacting in any environment that contains a liquid.

The tools or other apparatus disclosed herein may have all of the same properties and characteristics of the dissolvable composition described herein, as the tools or other apparatus are formed of the dissolvable composition. In certain aspects, the tools or other apparatus are formed exclusively of the dissolvable composition, such that the tools or other apparatus do not include or contain any other material other than the dissolvable composition. That is, composition 100 may constitute 100 wt. % of apparatus 500 based on a total weight of apparatus 500. In other embodiments, composition 100 constitutes less than 100 wt. % of apparatus 500, less than 90 wt. % of apparatus 500, less than 80 wt. % of apparatus 500, less than 70 wt. % of apparatus 500, less than 60 wt. % of apparatus 500, or less than 50 wt. % of apparatus 500, each based on a total weight of apparatus 500.

In some aspects, the tools are downhole tools, such as hydraulic fracturing balls (frac balls). In use, the frac balls may be injected downhole for fracturing a well. Upon contact with the liquid downhole (e.g., the drilling mud) the degradation of the composition begins. The time that it takes form the frac balls to fully dissolve may be controlled via: the thickness of the core material and each layer; the galvanic potential between the materials; the particular material constituents used to form the composition; relative amounts of each material (e.g., relative wt. %) within the composition; the arrangement of the materials (e.g., order of layers) within the composition; the size of the frac balls; the temperature down hole; and the pH downhole. By controlling the type, amount, and arrangement of the materials, the lifetime of the composition in a downhole environment can be controlled.

In other aspects, the tools or apparatus is a drone. In some aspects, the entirety of the drone is formed of the dissolvable composition. In other embodiments, the frame, body, and optionally other portions of the drone are formed of the dissolvable composition, while other portions of the drone are not formed of the dissolvable composition. In use, a drone formed of the dissolvable composition may be flown to a desired location (e.g., for intelligence surveillance in military applications). As the drone is at least partially degradable/dissolvable upon contact with moisture, the drone may be utilized as a disposable drone without risking discovery and/or retrieval by another. For example, typically a drone battery life limits the range of a drone. The drone may be flown to approximately have of its battery life, after which, the drone must either be returned to "base" or the drone will be at risk of failing over potentially enemy territory due to loss of battery power. However, with a dissolvable drone, the drone may be flown for the entirety of its battery life. The flight path of the drone may be planned such that at or towards the end of the flight path, the drone passes over a body of water. Thus, the drone may be purposefully flown into the water to dissolve upon contact therewith. As such, others attempting to retrieve the drone may be prevented from such retrieval.

In other aspects, the composition may be used to form electronics, medical equipment, disposable vehicles, or any other equipment where a controlled lifetime is required or desirable.

Figure 5A:
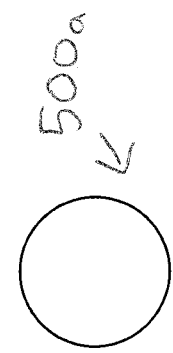
FIG. 5A depicts a frac ball in accordance with certain aspects of the present disclosure.
Figure 5D:
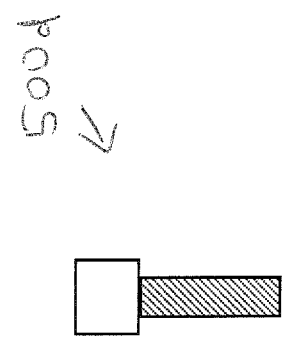
FIG. 5D depicts a medical implant in accordance with certain aspects of the present disclosure.
Figure 5C:
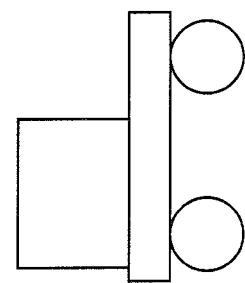
FIG. 5C depicts a land-based drone in accordance with certain aspects of the present disclosure.
Figure 5B:
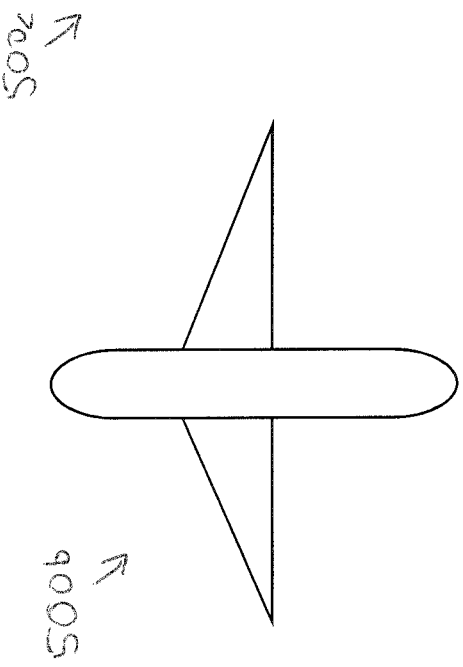
FIG. 5B depicts an aerial drone in accordance with certain aspects of the present disclosure.

FIG. 5A depicts frac ball 500a, FIG. 5B depicts aerial drone 500b, FIG. 5C depicts land-based drone 500c, and FIG. 5D depicts medical implant 500d (e.g., a screw).

Encapsulation

In some aspects, selection and arrangement of the layers of the multi-layer embodiments of the dissolvable composition provided herein allow for protection of the internal galvanic materials during processing, creation the galvanic cell, control of the galvanic reaction, control of the strength and other properties of the dissolvable composition and provision of water reactivity to dissolve portions of the material.

In certain aspects, the dissolvable composition includes a metals, ceramics, carbides, oxides, nitrides, or combinations thereof, which may be in the form of an encapsulation layer about the first material, the second material, the third material, or combinations thereof. In some embodiments, composition lacks any material between first material and second material, such that first and second material are in direct contact. In some embodiments, composition lacks any material between second material and third material, such that second and third material are in direct contact. In some embodiments, second material is the only material positioned between first and third materials within composition. In other embodiments, additional layers of additional materials are positioned between first and second materials, second and third materials, outside of third material, or combinations thereof.

Covalent Electrolytes

Without being bound by theory, pure water (e.g., distilled water) is a poor conductor of electricity because water is only slightly ionized. That is, only about two (2) out of every one (1) billion molecules in pure water ionize at 25° C. Water ionizes when one molecule of water gives up a proton to another molecule of water, yielding hydronium and hydroxide ions, as shown below.

$$H_2O(l) + H_2O(l) \rightleftharpoons H_3O^+(aq) + OH^-(aq)$$

In some cases, it has been found that solutions prepared from covalent compounds conduct electricity because the solute molecules react chemically with the solvent to produce ions. For example, pure hydrogen chloride is a gas consisting of covalent HCl molecules. This gas contains no ions. However, when hydrogen chloride is dissolved in water, the resultant solution is a good conductor. The water molecules provide an essential function in forming ions. For example, solutions of hydrogen chloride in many other solvents, such as benzene, do not conduct electricity and do not contain ions. Hydrogen chloride is an acid, and so HCl reacts with water, transferring H+ ions to form hydronium ions (H3O+) and chloride ions (Cl—), as shown below.

The reaction, above, is essentially 100% complete for HCl (i.e., HCl is a strong acid and, consequently, a strong electrolyte). Likewise, weak acids and bases that only react partially generate relatively low concentrations of ions when dissolved in water and are classified as weak electrolytes.

Reactions

Without being bound by theory, some of the reactions believed to occur during the galvanic reactions that result in dissolution of the composition provided herein are set forth below.

$$Mg(s)+2H+(aq)\rightarrow Mg_2+(aq)+H_2(g) \quad\quad a.$$

$$2Al(s)+6HCl(aq)\rightarrow 2AlCl_3(aq)+3H_2(g) \quad\quad b.$$

$$Ni+2HCl\rightarrow NiCl_2+H \quad\quad c.$$

Galvanic Electrochemical Reactions—E○(V)—Electrochemical Potentials

Some exemplary electrochemical potentials for Al and Ni are as follows:

$$Al_3+(aq)+3e\rightleftharpoons Al(s)-1.662$$

$$Ni_2+(aq)+2e\rightleftharpoons Ni(s)-0.25$$

For embodiments in which iron is used, iron reacts with oxygen and water as follows:

$$2Fe(s)+O_2(g)+H_2O(l)\rightarrow Fe(OH)_2(aq)$$

Material Strengths

TABLE 1

Properties of Example Composition (Comp 5).

| Comp 5 | Compressive (ultimate) | Ductility | Tensile |
|---|---|---|---|
| Cast | 33-35 ksi | 5-9% | 22-24 ksi |
| Forged | 52-56 ksi | 10-14% | 33-36 ksi |
| Forged/Extruded | 50-55 ksi | 12-15% | 50-54 ksi |

TABLE 2

Properties of Example Composition
(Comp 6, 3% chloride - KCl, NaCl, CaCl).

| Comp 6 | Compressive (ultimate) | Ductility | Tensile |
|---|---|---|---|
| Cast | 35-37 ksi | 5-7% | 20-22 ksi |
| Forged | 54-58 ksi | 8-12% | 30-32 ksi |
| Forged/Extruded | 53-55 ksi | 8-12% | 47-50 ksi |

TABLE 3

Properties of Example Composition
(Comp 6, 10% chloride - KCl, NaCl, NaCl).

| Comp 6 | Compressive (ultimate) | Ductility | Tensile |
|---|---|---|---|
| Forged | 55-60 ksi | 7-10% | 28-29 ksi |
| Forged/Extruded | 55-58 ksi | 7-11% | 45-49 ksi |

TABLE 4

Rates of Dissolution
(Solution = Distilled Water) of Example Compositions.

|  | 80 | 120 | 200 |
|---|---|---|---|
| Comp 5 | 7-14 mg/cm²/hr | 55-65 mg/cm²/hr | 85-101 mg/cm²/hr |
| Comp 6 (3% KCl) | 24-26 mg/cm²/hr | 75-83 mg/cm²/hr | 105-125 mg/cm²/hr |
| Comp 6 (10% KCl) | 50-70 mg/cm²/hr | 110-130 mg/cm²/hr | 170-190 mg/cm²/hr |

TABLE 4-continued

Rates of Dissolution
(Solution = Distilled Water) of Example Compositions.

|  | 80 | 120 | 200 |
|---|---|---|---|
| Comp 6 (10% NaCl) | 80-90 mg/cm²/hr | 125-150 mg/cm²/hr | 180-205 mg/cm²/hr |

Permutations

There are numerous variations in the arrangements and constituencies of the at least three materials of the dissolvable composition disclosed herein (the anode material, the cathode material, and the electrolytic material).

TABLE 5

Some Exemplary Variations in the Material Arrangements

|  | Particle 1 (Anode) | Particle 2 (Cathode) | Particle 3 |
|---|---|---|---|
| Ex. 1 | Uncoated | Uncoated | Uncoated |
| Ex. 2 | Uncoated | Uncoated | Coated |
| Ex. 3 | Uncoated | Coated | Uncoated |
| Ex. 4 | Coated | Uncoated | Uncoated |
| Ex. 5 | Coated | Uncoated | Coated |
| Ex. 6 | Coated | Coated | Uncoated |
| Ex. 7 | Coated | Coated | Coated |

Coated and uncoated, in Table 5, indicates that the particle is encapsulated with one oar more layers. In some aspects, particles 1 and 2 may be mixed, and then mixed with particle 3. In some aspects, particles 1 and 2 may be layered, and then mixed with particle 3. In some aspects, all particles may be mixed together. In some aspects, all particles may be layered together. Table 6 sets forth some additional combinations of particles that are possible.

TABLE 6

Some Exemplary Variations in the Material Arrangements

|  | Particle 1 (Anode) | Particle 2 (Cathode) | Particle 3 |
|---|---|---|---|
| Ex. 1 | Uncoated | Uncoated | Chloride Uncoated (accelerator) |
| Ex. 2 | Coated Particle | Uncoated | Chloride Uncoated |
| Ex. 3 | Uncoated | Coated | Chloride Uncoated |
| Ex. 4 | Coated | Coated | Chloride |
| Ex. 5 | Uncoated | Uncoated | Chloride/Coated |
| Ex. 6 | Combined with Particle 2 | Combined with Particle 1 | Chloride Coated and Uncoated |
| Ex. 7 | Multilayer particles combination of Particles 1 and 2 |  | Chloride |
| Ex. 8 | Combination of Particles 1, 2 and 3; Coated with Chloride or accelerated on particles or matrix parts |  |  |

Figure 6:
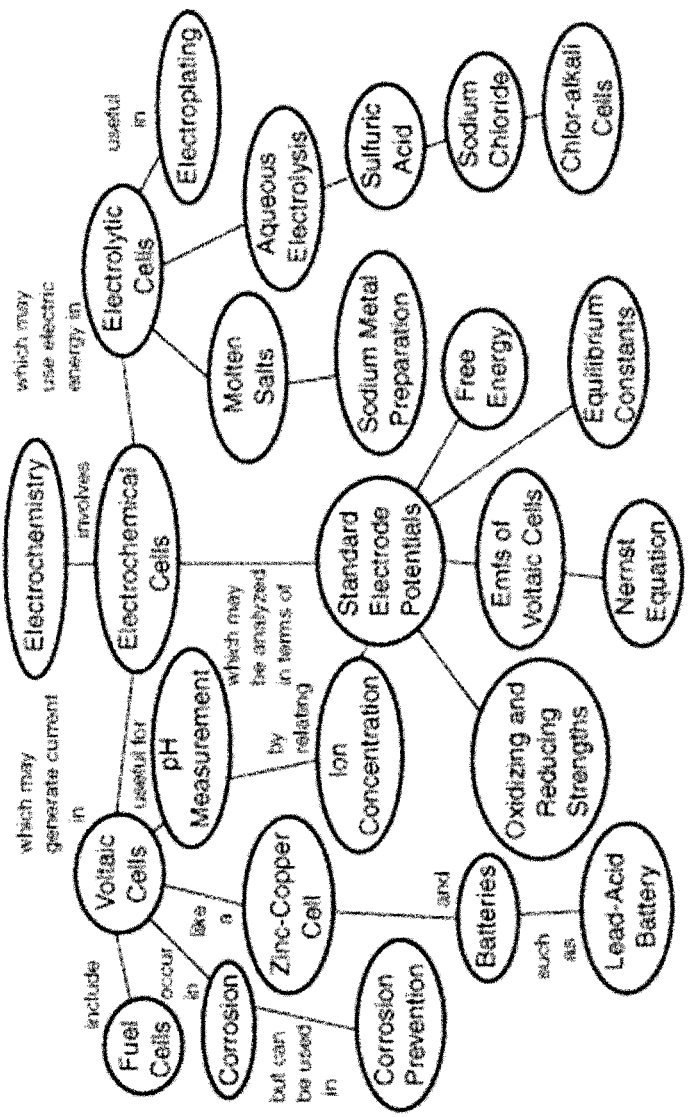
FIG. 6 sets forth various electrochemical reactions.

FIG. 6 sets forth some of the relevant electrochemical reactions that may occur between two galvanically reactive materials.

Figure 7B:
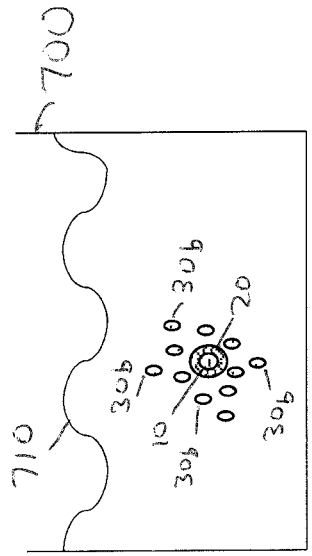
FIGS. 7A-7D depict the dissolution of a single particle of the composition within water.
Figure 7D:
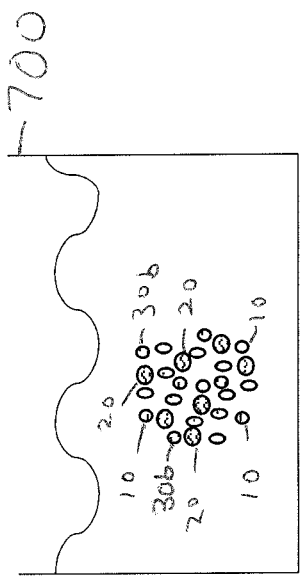
Figure 7A:
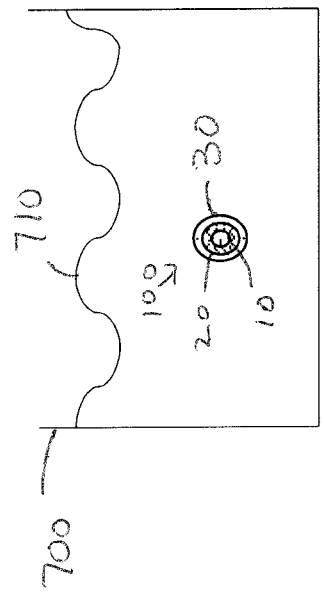
Figure 7C:
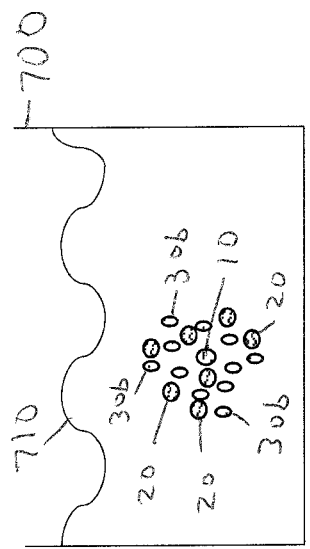

FIGS. 7A-7D depict the dissolution of a single particle of composition 100. One skilled in the art would appreciate that typically more than one particle of composition 100 would be present. However, for the purpose of simplicity and clarity, the dissolution of only one particle is described. With reference to FIG. 7A, a particle of composition 100 is placed into a local environment 700 (e.g., a tank or other contained water source) that contains water 710. Upon contact with water 710, electrolytic material 30 of composition 100 begins to dissolve within water 710. As shown in FIG. 7B, for at least a period of time dissolved electrolytic material 30 is more highly concentrated proximate to the location of the remainder of composition 100 (anode and cathode materials 10 and 20) than at other locations within water 710. Upon dissolution of electrolytic material 30, cathode material 20 is exposed to water 710 and ions formed by electrolytic material 30b, such that cathode material 20 begins to dissolve or separate within water 710. Upon dissolution of electrolytic material 30 and cathode material 20, anode material 10 is exposed to water 710, cathode material 20 and ions formed by electrolytic material 30b, such that anode material 10 begins to dissolve or separate within water 710.

Although the present embodiments and advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method comprising:
   providing a core particle comprising a first material;
   applying one or more coatings onto the core particle, wherein the one or more coatings comprise at least a second material, forming a coated core particle; and
   mixing a third material comprising electrolytic material with the coated core particle or coating the third material onto the coated core particle, forming a dissolvable composition;
   wherein the core particle and at least one coating thereon are electrochemically different such that the core particle and the at least one coating react in a galvanic reaction the presence of water and electrolytes, and wherein the third material is reactive with water to form an electrolyte, and wherein the first material forms an anode in the galvanic reaction and the second material forms a cathode in the galvanic reaction; and
   forming an aerial drone from the dissolvable composition, wherein the forming comprises spark plasma sintering (SPS), additive manufacturing, hot isostatic pressing (HIP), press-forging, or extruding.

2. A method comprising:
   providing an aerial drone, the aerial drone comprising a dissolvable composition, wherein the dissolvable composition comprises a first material, a second material, and a third material;
   contacting the aerial drone with water;
   wherein, upon or after contact with the water, the third material forms electrolytes, and wherein upon or after formation of the electrolytes the first material and the second material react in a galvanic reaction such that the aerial drone dissolves upon or after contact with water.

3. The method of claim 2,
   wherein the method includes flying the drone to a first location; wherein contacting the article with water includes landing the drone in the water.

4. An aerial drone, the aerial drone comprising:
   a dissolvable composition, wherein the dissolvable composition comprises a first material, a second material, and a third material;
   wherein the third material forms an electrolyte in water; and
   wherein the first material and the second material are electrochemically different such that the first material and the second material react, in a galvanic reaction, in the presence of water and electrolyte, such that the aerial drone dissolves upon or after contact with water.

5. The aerial drone of claim 4, wherein the dissolvable composition comprises:
   core particles, the core particles comprising the first material;
   coating layers disposed on outer surfaces of the core particles, the coating layers comprising the second material; and
   wherein the third material is in the form of coating layers disposed on outer surfaces of the second material or particles mixed with the core particles; and
   wherein the first material forms an anode in the galvanic reaction and the second material forms a cathode in the galvanic reaction.

6. The aerial drone of claim 5, wherein the third material is in the form of the particles that are mixed with the core particles.

7. The aerial drone of claim 5, wherein the third material is in the form of coating layers disposed on outer surfaces of the second material.

8. The aerial drone of claim 5,
   wherein the core particles comprise Mg or an alloy or ceramic thereof, Al or an alloy or ceramic thereof, Zn or an alloy or ceramic thereof, or Cu or an alloy ceramic thereof;
   wherein the coating layers of the second material comprise Ni or an alloy thereof, Fe or an alloy thereof, Ti or an alloy thereof, or a refractory metal or an alloy thereof; and
   wherein the third material comprises NaCl, CaCl, KCl, MgCl, or HCl.

9. The aerial drone of claim 5, wherein the first material forms from 60 to 98.5 weight percent (wt. %) of the dissolvable composition, wherein the second material forms from 0.5 to 30 wt. % of the dissolvable composition, and wherein the third material forms from 0.5 to 35 wt. % of the dissolvable composition, each based on a total weight of the dissolvable composition.

10. The aerial drone of claim 5, wherein the third material is chloride-based salt.

11. The aerial drone of claim 5, wherein the third material is an acid former.

12. The aerial drone of claim 5, wherein the third material is an alkali metal salt or an alkaline earth metal salt.

13. The aerial drone of claim 5, wherein the third material is a chloride, an oxide, or a nitride.

14. The aerial drone of claim 5, wherein the galvanic reaction occurs at a pH below 11.

15. The aerial drone of claim 5, wherein the galvanic reaction occurs upon contact with distilled water.

16. The aerial drone of claim 5, wherein the core particles comprise Mg-core particles, wherein the coating layers of the second material comprise inner layer coatings of Ni disposed about the Mg-core particles, and wherein coating layers of Al are disposed about the inner layer coatings of Ni as a fourth material of the composition.

17. The aerial drone of claim 16, wherein the third material is in the form of coating layers of a chloride salt disposed about the coating layers of Al, or wherein the third material is in the form of chloride salt particles mixed with the coated Mg-core particles.

18. The aerial drone of claim 17, wherein the chloride salt particles are coated with Ni, Cu, Al, or Mg.

* * * * *